United States Patent [19]

Uijttewaal et al.

[11] Patent Number: 4,584,127

[45] Date of Patent: Apr. 22, 1986

[54] UTILIZATION OF 1-CYCLOPENTENYLACETIC ACID AS PERFUMING INGREDIENT

[75] Inventors: Arnoldus Uijttewaal, Geneva; Dietrich Kastner, Givrins, both of Switzerland

[73] Assignee: Firmenich SA, Switzerland

[21] Appl. No.: 570,177

[22] Filed: Jan. 12, 1984

[30] Foreign Application Priority Data

Jan. 26, 1983 [CH] Switzerland ........................... 419/83

[51] Int. Cl.[4] ............................................... A61K 7/46

[52] U.S. Cl. ................................ 252/522 R; 252/8.6; 252/174.11; 424/69; 424/70

[58] Field of Search ............... 252/8.6, 174.11, 522 R; 424/69, 70

[56] References Cited

U.S. PATENT DOCUMENTS 1,965,792 7/1934 Chaux ........................ 252/522 R X
4,031,132 6/1977 Naegli ................................ 562/504
4,280,934 7/1981 Schulte-Elte .................. 252/522 R

OTHER PUBLICATIONS

Horclois, CA 29:141[4], (1935).

*Primary Examiner*—Thomas A. Waltz
*Attorney, Agent, or Firm*—Scully, Scott, Murphy & Presser

[57] ABSTRACT

1-Cyclopentenylacetic acid, a compound of formula

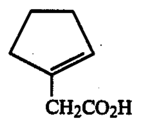

possesses useful odorous properties and consequently can find an advantageous application for the preparation of perfume compositions, perfume bases and perfumed products.

3 Claims, No Drawings

UTILIZATION OF 1-CYCLOPENTENYLACETIC ACID AS PERFUMING INGREDIENT

BRIEF SUMMARY OF THE INVENTION

The invention relates to a method to enhance, improve or modify the odorous properties of perfumes, perfume bases and consumable materials which comprises adding therein an odor modifying amount of 1-cyclopentenylacetic acid of formula

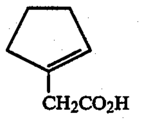

The invention relates further to a perfume, a perfume base and a perfumed consumable material characterized in having added therein an odor modifying amount of 1-cyclopentenylacetic acid.

This invention provides also a method to confer or enhance the honey-type odor character of perfumes and perfume bases which comprises adding thereto an odor modifying amount of 1-cyclopentenylacetic acid.

BACKGROUND OF THE INVENTION

Among the variety of current perfume ingredients, very few are the compounds able to confer the so-called "honey" odor character to the compositions or consumable materials to which they are added. Among them, the most commonly known one is certainly phenylacetic acid whose scent is sweet of animal and honey-type [see S. Arctander, Perfume and Flavor Chemicals, Sec. 2492, Montclair N.J., USA (1969)]. Its animal note however is considered as being too pronounced and consequently its utilization raises certain problems to perfumers who have to seek proper accord in order to harmonize the overall composition.

We have now discovered that 1-cyclopentenylacetic acid possesses the typical honey note without however the secondary characters of phenylacetic acid and that, consequently, it could be used successfully to confer such a character to perfumes and perfume compositions or bases, or to perfume a variety of consumable materials.

PREFERRED EMBODIMENTS OF THE INVENTION

Owing to the fact that 1-cyclopentenylacetic acid possesses a very good strength and an excellent substantivity, it finds a utilization in a wide spectrum of applications both in the area of fine perfumery, such as alcoholic compositions, and in the area of technical or functional perfumery. Thus, it can be used to perfume consumable materials such as soaps, powder or liquid detergents, fabric softeners, waxes and household articles. It can also be used to perfume shampoos, bath foam preparations or body and moisturizing creams.

In fact, any material to which an agreable scent confers a degree of pleasantness for the consumer could be perfumed with the compound of the invention.

The proportions at which it can be used to develop the desired effects can vary in a wide range of values. Concentrations of the order of 1°–10°/$_{oo}$ by weight, based on the total weight of the composition or perfumed article to which it is added, are often sufficient to achieve positive results.

Concentrations of 0.1–2% are used preferably in the manufacture of concentrated compositions or "coeurs". The current perfuming techniques are used also in the present case. Thus, 1-cyclopententylacetic acid can be added either directly to the material it is desired to perfume or, more often, as a solution in the usual solvents, diluents or supports, in combination or not with other perfume coingredients.

1-Cyclopentenylacetic acid is a new chemical entity. It can be prepared according to known methods [see U.S. Pat. No. 1,965,792]. Alternatively, it can be synthesized from methyl cyclopentylidene-acetate [see U.S. Pat. No. 4,280,934] via hydrolysis, following the reaction pathway given hereinbelow:

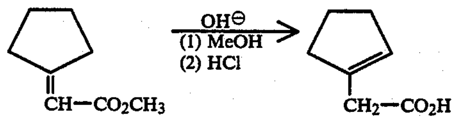

A detailed description of the method used follows.

To a solution of the methyl ester (700 g) in 2 l of methanol, there was added dropwise at reflux (70° C.) a 30% aqueous solution of NaOH.

The reaction mixture was kept at 70° C. for 1 h, then 2.5 l of water were added thereto and the methanol was evaporated. After acidification with HCl, separation of the organic phase followed by reextraction with ether of the mother liquor, the two combined organic phases were distilled at reduced pressure. The desired product was obtained with a yield of 82,3% at b.p. 96° C./6.65 Pa ca. Traces of the isomeric acid of formula

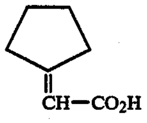

were detected in the product thus obtained, however its presence did not exert any adverse influence on the odor quality of the main product.

It is worth mentioning that above cited U.S. Pat. No. 1,965,792 describes the use of certain esters of the acid in question as perfuming ingredients. The useful properties of the acid escaped however the attention of the patentee who neither suspected nor suggested the specific utilization disclosed in the instant application.

The invention is illustrated in a more detailed manner in the following examples.

EXAMPLE 1

100 G of soap chips are mixed with 2 g of 25% by weight solution of 1-cyclopentenylacetic acid in diethyl phthalate until complete homogeneity. The resulting mass was heated under pressure at 160° C. for 10 h and the resulting liquid was poured into molds. The resulting soap bar showed a distinct honey-type scent.

EXAMPLE 2

A base rose-type composition was prepared by mixing the following ingredients (parts by weight):

| | |
|---|---|
| Citronellol | 30 |

-continued

| | |
|---|---|
| Geraniol | 20 |
| Phenethylol | 20 |
| Rose oxide 10%*[1] | 4 |
| β-Damascenone 1%*[1] | 2 |
| Phenylacetaldehyde 10%* | 6 |
| β-Dorinone* 50%[1] | 2 |
| Citronellyl acetate | 2 |
| Eugenol | 2 |
| Linalol | 6 |
| Terpineol | 6 |
| Total | 100 |

*in dipropylene glycol
[1]origin: Firmenich SA, Geneva

The addition of 0.5 parts by weight of 1-cyclopentenylacetic acid to the above composition conferred to it a sweeter, rounder and more lifting odor.

EXAMPLE 3

A base perfume composition destined to be incorporated in a shampoo was prepared by mixing the following ingredients (parts by weight):

| | |
|---|---|
| Hexylcinnamaldehyde | 150 |
| Cinnamic alcohol | 100 |
| Terpineol | 100 |
| Bee-wax abs. 10%* | 100 |
| Cyclosia Base[1] [4] | 80 |
| Ethyl malonate | 80 |
| Phenethylol | 60 |
| Hydratropic alcohol | 60 |
| Dodecyl acetate | 60 |
| Hedione ®[1] [5] | 40 |
| Cyclohexylethyl acetate | 40 |
| Nerolidol | 40 |
| Ethyl phenyl acetate | 20 |
| Glycomel[1] [2] | 20 |
| Farnesol | 20 |
| Mayol ®[1] [3] | 20 |
| Total | 990 |

*in dipropylene glycol
[1]origin: Firmenich SA, Geneva
[2]methyl 3-methyl-3-(norbornen-5-yl)-glycidate
[3]4-isopropylcyclohexylmethanol
[4]hydroxycitronellal
[5]methyl dihydrojasmonate The addition of 10 parts by weight of 1-cyclopentenylacetic acid to the above composition conferred thereto a marked honey scent. Its sweet character is specially adapted to perfume baby shampoos.

EXAMPLE 4

1-Cyclopentenylacetic acid at 10% solution in diethyl phthalate was used to perfume several consumable materials. The odor stability and the color effect of the thus obtained perfumed materials was examined under the conditions described hereinbelow.

| Perfumed material | Concentration[1] (w/w) | Temp. (°C.) 1 month exposure | Results* stability/ coloration |
|---|---|---|---|
| Eau de Cologne | 5% in EtOH | 40 | S/N |
| Cream | 0.4% | 40 | S/N |
| Shampoo | 0.5% | 40 | S/N |
| Deodorant (aerosol) | 1.2% | 40 | S/N |
| Hair lac | 0.3% | 40 | S/N |
| Soap | 0.5% | 40 | S/N |
| Talc | 0.5% | 40 | S/N |
| Powder detergent | 0.2% | 40 | S/N |
| Chlorinated dishwashing powder | 0.2% | 40 | S/N |

*S = stable;
N = normal
[1]expressed as weight of the 10% solution.

The odor stability was also confirmed by prolonged UV irradiation essays.

What we claim is:

1. A method to enhance, improve or modify the odorous properties of perfumes, perfume bases and consumable materials which comprises adding therein an odor modifying amount of 1-cyclopentenylacetic acid of formula

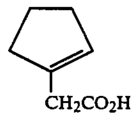

2. A perfume, a perfume base and a perfumed consumable material characterized in having added thereto an odor modifying amount of 1-cyclopentylacetic acid.

3. A method to confer or enhance the honey-type odor character of perfumes and perfumed bases which comprises adding thereto an odor modifying amount of 1-cyclopentenylacetic acid.

* * * * *